United States Patent [19]

Jang

[11] Patent Number: 4,990,139

[45] Date of Patent: Feb. 5, 1991

[54] TANDEM INDEPENDENTLY INFLATABLE/DEFLATABLE MULTIPLE DIAMETER BALLOON ANGIOPLASTY CATHETER SYSTEMS

[76] Inventor: G. David Jang, 204 E. South St., Redlands, Calif. 92373

[21] Appl. No.: 514,156

[22] Filed: Apr. 25, 1990

Related U.S. Application Data

[63] Continuation of Ser. No. 232,916, Aug. 16, 1988, abandoned, which is a continuation of Ser. No. 905,840, Sep. 10, 1986, Pat. No. 4,763,653.

[51] Int. Cl.$^5$ ............................................. A61M 25/10
[52] U.S. Cl. .................................... 604/101; 606/192
[58] Field of Search ...................... 606/191, 192, 194; 600/1; 604/96–103

[56] References Cited

U.S. PATENT DOCUMENTS

| | | | |
|---|---|---|---|
| 3,411,506 | 11/1968 | Velasco | 606/192 |
| 4,271,839 | 6/1981 | Fogarty et al. | 606/194 |
| 4,527,549 | 7/1985 | Gabbay | 604/101 |
| 4,630,609 | 12/1986 | Chin | 604/101 |
| 4,655,746 | 4/1987 | Daniels et al. | 604/101 |

FOREIGN PATENT DOCUMENTS 654214 2/1986 Switzerland .

Primary Examiner—Stephen C. Pellegrino
Assistant Examiner—William Lewis
Attorney, Agent, or Firm—Knobbe, Martens, Olson & Bear

[57] ABSTRACT

Disclosed is a catheter for performing balloon angioplasty having multiple independently inflatable/deflatable balloons thereon, each balloon having a different diameter. The balloons are capable of withstanding pressures in excess of 100 psi and are non-elastomeric and imperforate. Also disclosed is a method for performing balloon angioplasty by advancing a balloon catheter of the type disclosed into a stenosis inside a blood vessel, inflating a first balloon to partially dilate the stenosis, advancing a second balloon into the partially dilated stenosis, wherein the diameter of the second balloon is greater than the diameter of the first balloon, and inflating the second balloon to further dilate the stenosis. Also disclosed is a method for performing balloon angioplasty with a catheter of the type disclosed herein, by positioning a first balloon inside a first stenosis in a blood vessel and inflating a first balloon to dilate the first stenosis, and positioning a second balloon inside a second stenosis in a blood vessel and inflating the second balloon to dilate the second stenosis, wherein the diameter of the first balloon is different from the diameter of the second balloon. A third stenosis may be dilated with a third balloon on the catheter in a similar manner, where the third balloon has a diameter different from that of the other two balloons.

2 Claims, 8 Drawing Sheets

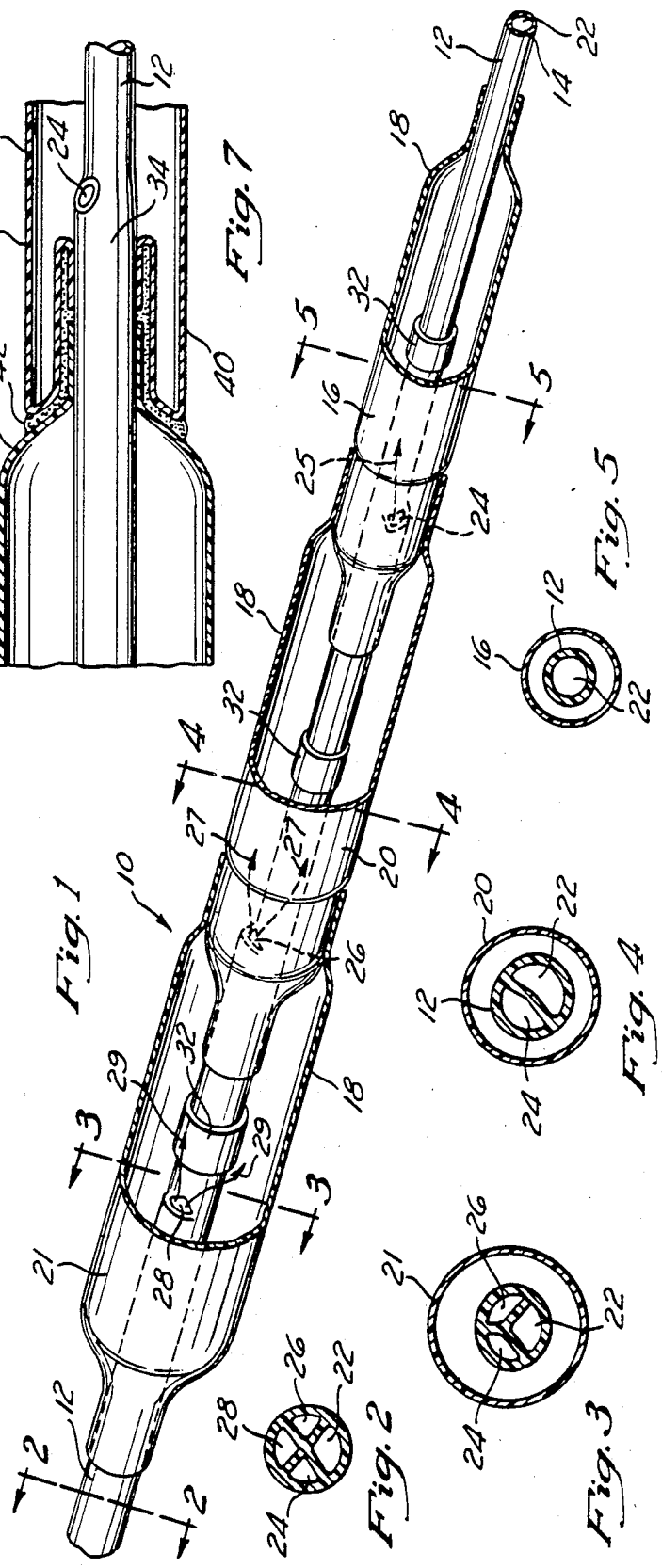

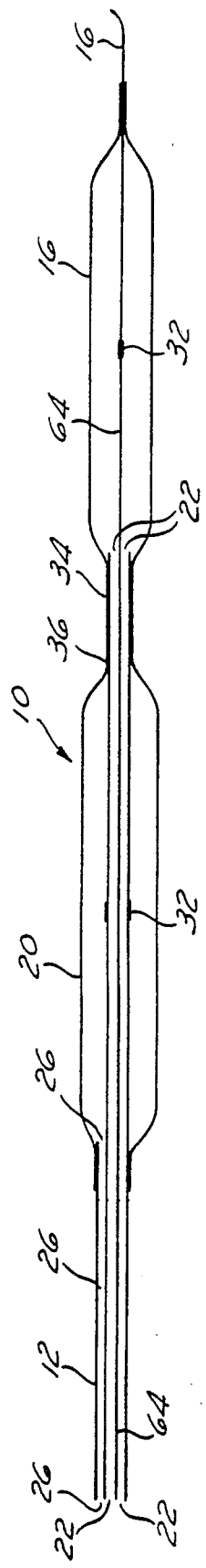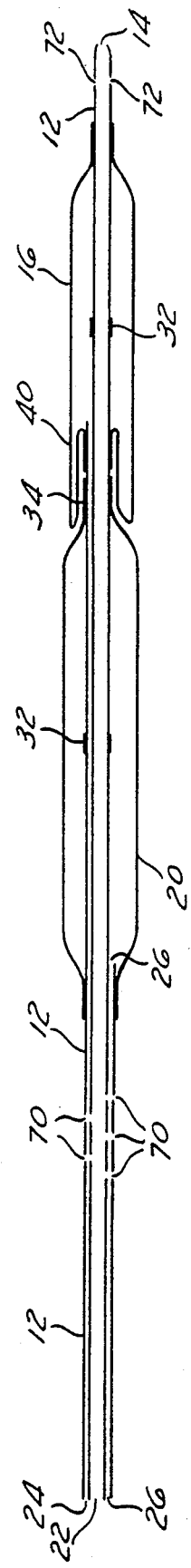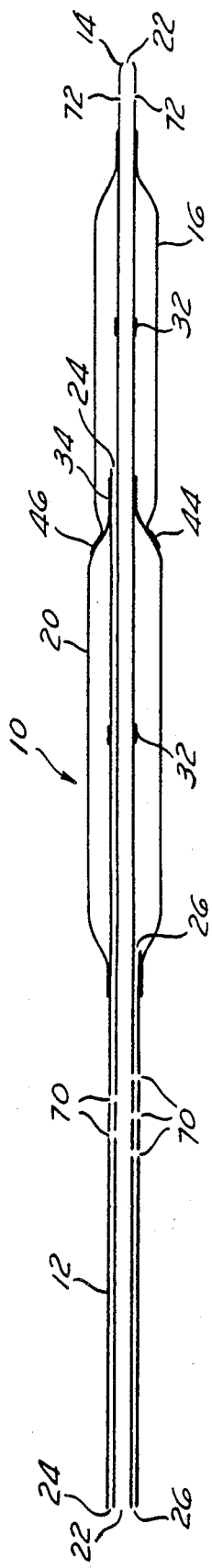

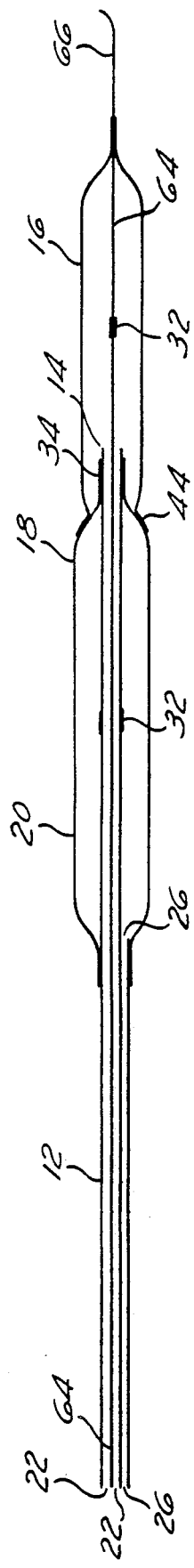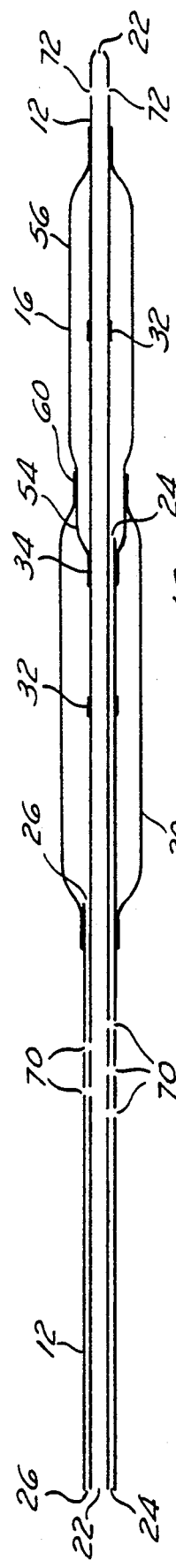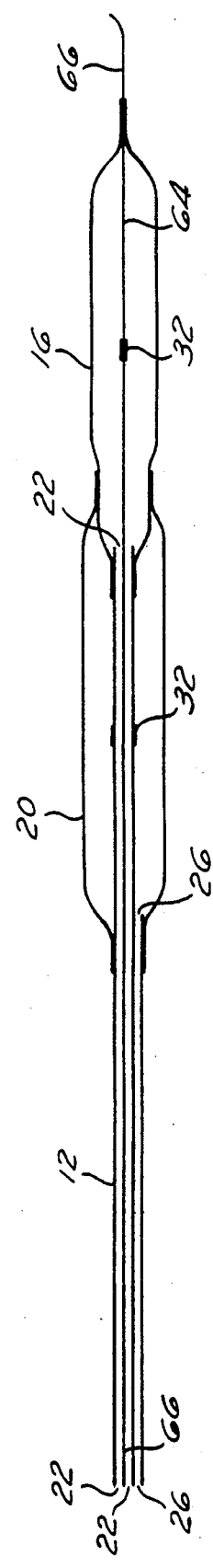

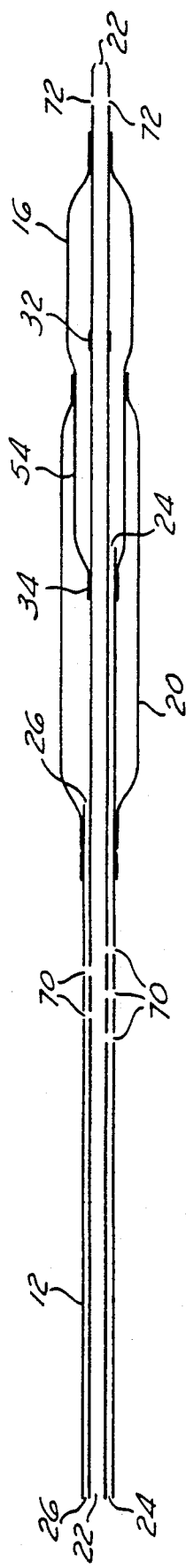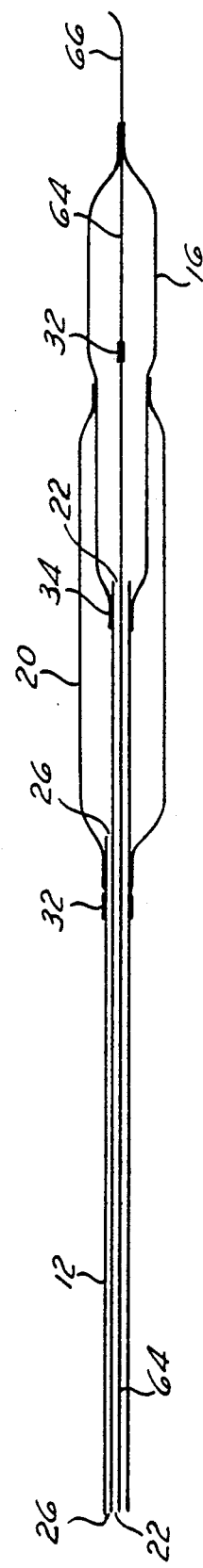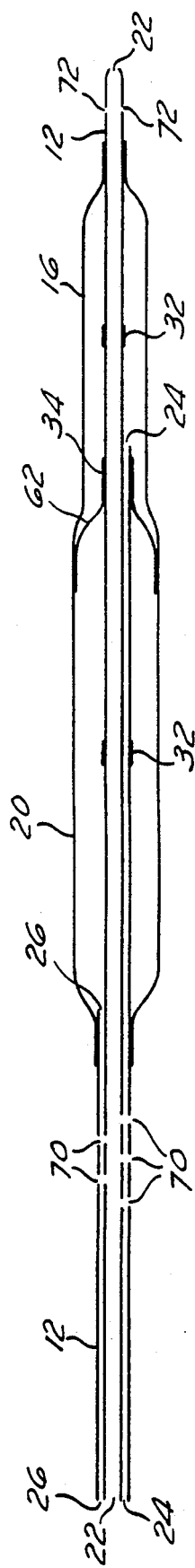

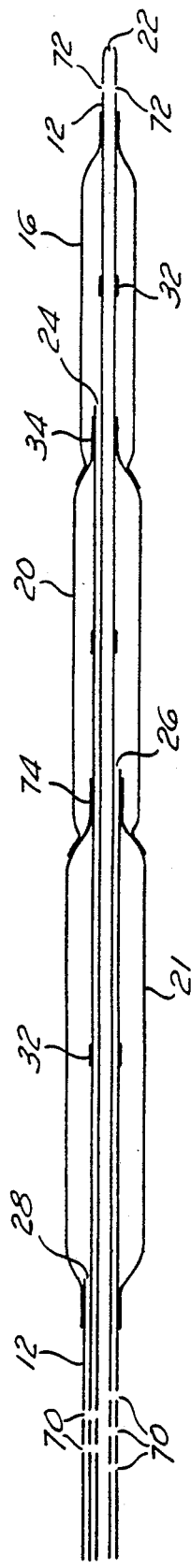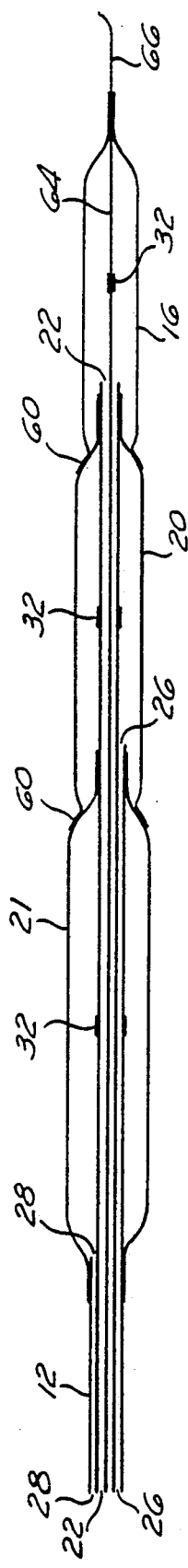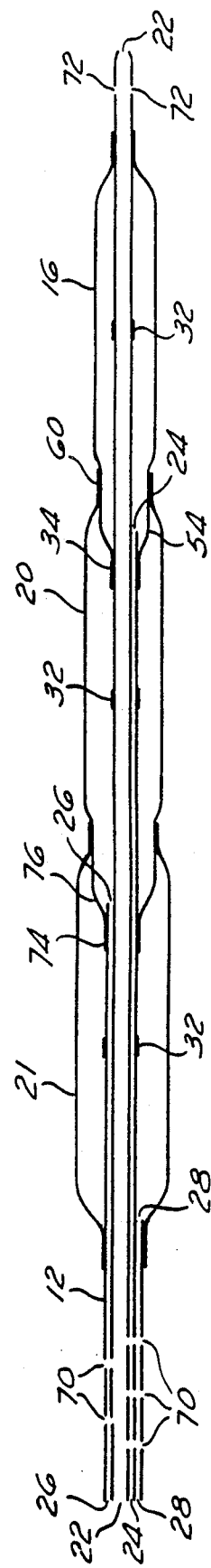

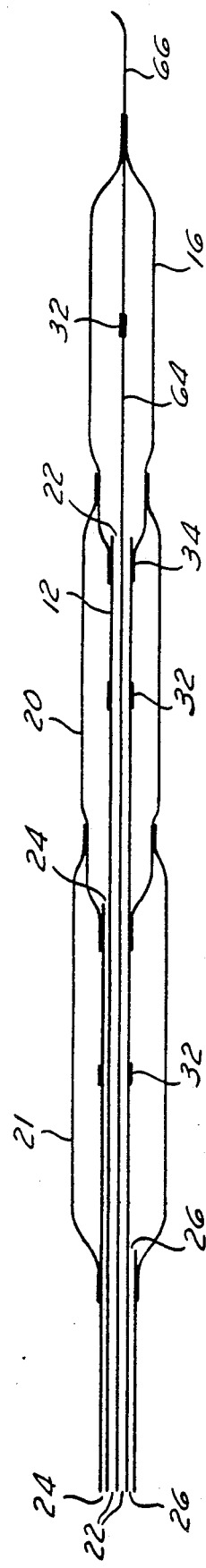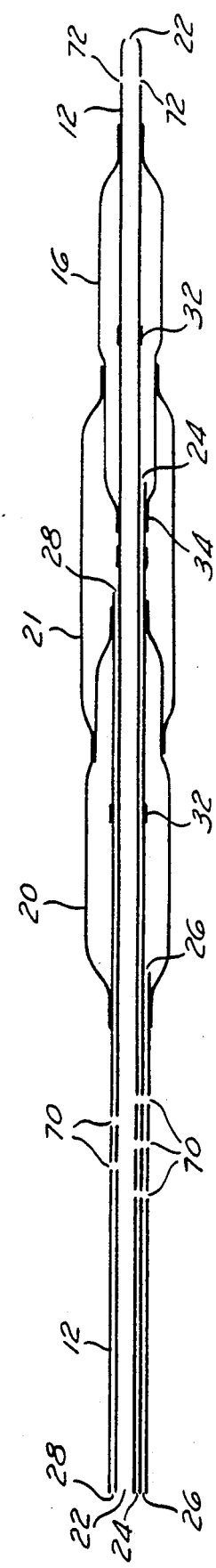

TANDEM INDEPENDENTLY INFLATABLE/DEFLATABLE MULTIPLE DIAMETER BALLOON ANGIOPLASTY CATHETER SYSTEMS

This is a continuation of application Ser. No. 232,916, filed Aug. 16, 1988, now abandoned, which is a continuation of Ser. No. 905,840, filed Sept. 10, 1986, now U.S. Pat. No. 4,763,653.

BACKGROUND OF THE INVENTION

This invention relates to balloon angioplasty, and particularly to angioplasty catheter systems utilizing multiple balloons and to angioplasty procedures utilizing those catheters.

Coronary angioplasty has emerged as the only viable present alternative to bypass surgery for revascularization of stenotic and occluded coronary arteries. Although transluminal angioplasty has application in peripheral artery disease, it is most widely used in the treatment of coronary artery disease. Unlike bypass surgery, percutaneous angioplasty does not require general anesthesia, cutting of the chest wall, extracorporeal perfusion or transfusion of blood. Percutaneous coronary angioplasty is not only less invasive and less traumatic to the patient, it is also less expensive because the angioplasty patient will have a shorter hospital stay and shorter post-procedure recovery time.

Percutaneous transluminal angioplasty is performed by making a skin puncture with a specially-designed needle in one of the groins, and then introducing a guiding catheter (typically 8 or 9 French size) into the aorta and coronary artery orifice. A smaller caliber catheter which has a built-in inflatable and deflatable balloon of predetermined size and diameter is passed through the guiding catheter which is positioned in the opening of a target artery. This balloon catheter (with the balloon totally deflated by negative pressure) is advanced inside the target artery toward the point of obstruction that needs to be dilated. With the balloon portion of the catheter properly positioned inside the obstructed segment of the artery, under X-ray fluoroscopic observation, the balloon is inflated by injecting contrast media mixed with saline at a pressure sufficient to overcome the resistance of the atherosclerotic plaque of the obstructed segment.

During the guiding catheter manipulation and especially while the balloon catheter is being advanced into the narrowed segment of the artery, X-ray fluoroscopy is used extensively. However, because one cannot ordinarily see the anatomy of an artery under X-ray fluoroscopy, contrast material is used. When contrast media is injected into an artery, details of the arterial anatomy are briefly visible until the contrast material flows away with the blood flow through the artery. Radiographic arteriograms are recorded during that brief moment of visualization. If the anatomic structures are complex and negotiating a particular arterial channel with the balloon catheter is difficult, frequent contrast injections during the procedure are necessary. However, there are limits to the amount of contrast material one can use in a given patient. For instance, the upper limit of Renografin-76 in a normal individual is approximately 3 c.c.'s per kilogram of body weight. The tolerance of a physically-ill individual may be substantially less. Excessive amounts of contrast material can be toxic to the kidneys, liver, and brain.

By inflating the balloon multiple times over a period of between 20-30 seconds and one or two minutes (allowing blood flow between inflations), the desired dilation of the obstructed segment of the artery can be achieved. When the desired results have been obtained by balloon inflations, the guiding catheter and the balloon catheter (with the balloon completely deflated with negative pressure) are withdrawn from the artery and the procedure is successfully terminated.

Atherosclerotic coronary artery disease is not curable. Both bypass surgery and balloon angioplasty are considered palliative treatments. Recurrence of disease after bypass surgery or coronary angioplasty is prevalent, and repeat procedures are not uncommon due to the nature of the disease. A patient may initially develop single-vessel coronary artery disease and then slowly progress into multiple-vessel disease over the years. Bypass surgery or angioplasty do help to relieve the symptoms, but they generally cannot prevent a gradual progression of the disease.

Because the cost of bypass surgery is 2 to 2.5 times the cost of angioplasty, and because bypass surgery is more invasive, more traumatic, requiring longer hospital stays and longer post-operative recuperation, future demand for angioplasty is expected to grow as the physician skills and equipment technology expands. It has been estimated that the number of coronary artery angioplasties performed in the United States will double or triple to 450,000 or 500,000 cases per year by the early to mid 1990's. It also has been estimated that the number of multiple-vessel angioplasty cases will be from 2 to 2.5 times the number of single-vessel angioplasty cases. This will be a dramatic change from the situation in 1986 in which 70 to 80 percent of the coronary angioplasty cases are single-vessel dilations. The expected future growth of multi-vessel coronary angioplasty has serious technical and patient care implications. Present-day coronary angioplasty technology is based on the original single balloon concept which was designed to tackle single-vessel disease and thus single-vessel dilations. However, the single balloon technology is inadequate to meet the requirements of most multi-vessel disease situations.

During a typical coronary angioplasty, most of the procedure time is spent in certain preliminary steps that are necessary before the balloon can be inflated inside the obstructed segment of a target artery. In fact, the real job of dilating a vessel takes less than 20 percent of the total procedure time. The preliminary steps include patient (aseptic) preparation, groin preparation and needle puncture, insertion of the guidewire into the artery to introduce the guiding catheter, arterial heparinization, manipulation of the guiding catheter to cannulate the target coronary orifice, preliminary arteriography using contrast media injection into the artery and taking radiographic cine. Moreover, the balloon catheter must be prepared before it can be introduced into the target artery through the lumen of the guiding catheter. Preparation of the balloon catheter takes a minimum of 15-20 minutes. X-ray fluoroscopy and contrast media are extensively used during the guiding catheter and balloon catheter manipulations, especially when the balloon tip is being manipulated through the inside of the artery toward an obstructed segment which needs to be reopened by the balloon tip. Sometimes, the majority of the procedure time and the limits of the total allowable contrast volume are used up at this phase of a procedure. It is clear from the medical literature that the longer the procedure, the greater the risk of complications during cardiac catheterization. Likewise, the larger the volume of contrast material, the greater the chance of kidney failure or tissue toxicity, including brain and/or liver damage.

The size and diameter of the balloon to be used in a transluminal angioplasty should be approximately matched to the size and native diameter of the obstructed segment of the artery to be dilated. If the balloon size and diameter is smaller than the native artery, the results of balloon angioplasty are suboptimal, requiring a second dilation with a larger-sized balloon. In some cases, the result is a failed procedure, which may require either a second separate angioplasty procedure (especially if too much contrast material was already used) or bypass surgery. If the balloon is oversized in relation to the obstructed segment of the native vessel, the inner wall of the artery may dissect from the remainder of the artery and may occlude the vessel completely, causing total cessation of blood flow to the target area of the myocardium. This complication, except in rare occasions, leads to acute myocardial infarction and necessitates emergency bypass surgery. If the acute occlusion leads to a large infarction, death is a possibility.

The most common balloon diameters in demand for coronary angioplasties are 2.0 mm, 2.5 mm, 3.0 mm and 3.5 mm. The 2.0 mm and 2.5 mm balloons are used in patients with small caliber coronary arteries or in the distal coronary branches of patients with otherwise normal-sized coronary arteries. The 3.0 mm and 3.5 mm balloons are generally used in the proximal and larger native coronary arteries. If a patient has a single obstruction in the right or left coronary artery system, a single balloon catheter with a matching diameter and size will be selected for the intended dilation procedure. When the balloon is inflated inside the obstructed segment of the native artery, the balloon should maintain the original preshaped configuration and diameter under the maximum allowed pressure, which is generally up to 150 psi. Polymers such as PVC (polyvinylchloride) and various derivatives of polyethylene have proved to be suitable for making balloon catheters for coronary angioplasty. New polymer derivatives, including variations of Mylar material, are gaining popularity because of their high tensile strength and their potential for making very thin-walled dilation balloons.

In single lesion dilations, the choice of a properly-sized balloon catheter is relatively simple, although there are instances in which the original selection of the balloon catheter is inadequate so that a second balloon catheter is necessary to complete the procedure successfully. However, in multi-vessel disease, balloon catheter selection becomes compounded and complex. For example, a patient may have three lesions in his left coronary artery, and all three lesions may be approachable individually for successful balloon angioplasty. But such lesions may be in vessels of different sizes such as a 3.0 mm lesion in the proximal portion of the left anterior descending artery (LAD), a 2.0 mm lesion in the distal segment of the LAD, and a 2.5 mm lesion in the superior obtuse marginal artery. With currently available balloon catheters, angioplasty of these three differently-sized lesions is not always impossible, but it is cumbersome and inefficient. For each lesion, a matching balloon catheter is exchanged and manipulated into the target lesion under fluoroscopy with numerous contrast injections. To do this three times in a row requires roughly three times the procedure time, three times the contrast amount, and a minimum of three separate balloon catheters and their accessory devices. In light of the forecast that approximately two thirds of 450,000 to 500,000 patients in the 1990's will need multi-vessel coronary angioplasty, it is clear that there is a need for a major advance in balloon angioplasty that will provide more efficient and cost effective angioplasty balloon systems specifically designed (and suited) for multi-vessel coronary angioplasty.

SUMMARY OF THE INVENTION

The present balloon angioplasty catheter invention is specifically designed for dilation of multiple vessels of different sizes. The present invention also includes a method of using this new catheter in performing multi-vessel angioplasty procedures in a much shorter time and at significantly reduced risk to the patient than is possible with prior art technology.

The catheter of the present invention is a multi-lumen catheter bearing a plurality of individually inflatable and deflatable balloons of predetermined, different sizes. The balloons are mounted in tandem on the catheter shaft so that a smaller balloon is bonded to the distal end of the catheter just distally of a larger, separately inflatable balloon.

The present invention is designed for compatibility with existing and commercially available guidewires and guiding catheters, requiring, at most, minimal modification of those existing systems.

The balloons utilized in the present invention must meet stringent requirements that are unique to angioplasty balloons. They are: (a) the balloon must maintain its predetermined precise diameter and its original configuration under high inflation pressures (typically up to 150 psi or more) without significant or undue stretch or deformation; (b) the material used in construction of the balloon must have a high tensile strength and not rupture during inflation to the prescribed high pressure; (c) the balloon must be inflatable and deflatable under the external control of the operator; (d) the cross-sectional profile of the balloon should be low (0.035" to 0.065" or less in diameter) when it is deflated with negative pressure so that it can pass through the tight and sometimes very hard internal lumen of the stenotic segment of a target artery; and (e) the material must be flexible as well as resilient so that the balloon catheter can negotiate the tortuous and sometimes irregular artery by following or advancing over a guidewire already placed in the artery ahead of the balloon catheter.

Thus, in accordance with one embodiment of the present invention, there is provided a catheter for performing balloon angioplasty, comprising an elongate, flexible catheter shaft having a plurality of lumens therethrough, and a plurality of imperforate angioplasty balloons on the shaft, with the interior of each of the balloons connected to a different lumen for separate inflation and deflation of the balloon. Each of the balloons has an inflatable portion having a predetermined maximum inflated diameter and is formed of non-elastomeric material. Each balloon is capable of substantially maintaining the predetermined maximum inflated diameter at inflation pressures of 100 psi, preferably 150 psi, and most preferably 200 psi. The balloons on the catheter are generally cylindrical and comprise a first balloon on the catheter shaft near the distal end thereof, and a second balloon on the catheter shaft proximally of and adjacent to the first balloon. The maximum inflated diameter of the second balloon is greater than the maximum inflated diameter of the first balloon. In accordance with one embodiment of the invention, an attachment site is provided on the catheter shaft between the first balloon and the second balloon, to which the proximal end of the first balloon or the distal end of the second balloon, or both, are attached. At least a part of the inflatable portion of one of said balloons is over the attachment site.

In one embodiment of the present invention, the catheter shaft has a central lumen extending longitudinally therethrough for receiving a steerable guidewire of conventional design. The catheters of the present invention may further comprise a lumen for permitting the flow of blood through the catheter shaft past the balloons. This lumen is preferably the central lumen.

In accordance with another embodiment of the present invention, an axial torque guidewire extends through the catheter shaft and out of the distal end thereof, and the proximal end of the first balloon is bonded to the distal end of the catheter shaft, and the distal end of the first balloon is bonded to the wire.

In accordance with another aspect of the present invention, a third balloon is provided on the catheter shaft proximally of but adjacent to the second balloon. The maximum inflated diameter of the third balloon is greater than the maximum inflated diameter of the second balloon. Thus, the diameter of the balloons on the catheter preferably increases from the distal balloon to the proximal balloon. The three-balloon catheter may be provided with an axial torque guidewire extending through the catheter shaft and out of the distal end of the catheter shaft, and the distal end of the first balloon may be bonded to the wire with the proximal end of the first balloon and both the proximal and distal ends of the second and third balloons bonded to the catheter shaft.

In accordance with another embodiment of the three-balloon catheter, the catheter extends through the first, second, and third balloons, and a central lumen extends through the catheter shaft for receiving a steerable guidewire. Holes may be provided in communication with a lumen, preferably the central lumen, for permitting the flow of blood through the catheter shaft past the balloons.

In one embodiment of the three-balloon catheter, an attachment site is provided on the catheter shaft to which the proximal end of the first balloon and the distal end of the second balloon are joined, wherein either the first balloon or the second balloon has been formed to at least partially prolapse over the attachment site. The prolapsed balloon is preferably the distal, first balloon, and it preferably prolapses over substantially the entire attachment site. The first balloon may be permanently formed into the prolapsed shape, and also may be bonded to the attachment site to hold it into the prolapsed shape. Similarly, the second balloon may be prolapsed back over the site where the proximal end thereof is bonded to the catheter shaft.

In another embodiment of the invention, two of the balloons are formed from the same piece of material with a narrow waist connecting them. This narrow waist of balloon material is attached to the central attachment site.

In another embodiment of the catheter of the present invention, the distal end of the second balloon is attached to the central attachment site on the catheter shaft, and the proximal end of the first balloon is attached to the wall of the second balloon proximally of the central attachment site on the catheter shaft. The proximal end of the second balloon may be attached to the wall of the third balloon in a similar manner. Steerable guidewires, bypass sideholes, or axial torque guidewires may be provided in any of these embodiments.

Any of the two-balloon catheters of the present invention may be constructed so that the distal end of the second balloon is bonded to the wall of the first balloon distally of the proximal end of the first balloon, so that the first balloon is partially inside the second balloon. In one embodiment of this particular catheter, the maximum inflated diameter of the portion of the first balloon inside the second balloon is less than the maximum inflated diameter of the portion of the first balloon outside of the second balloon by an amount approximately equal to the thicknesses of the second balloon overlying the first balloon when the first balloon is inflated and the second balloon is uninflated. Thus, when the second balloon is deflated and the first balloon is inflated, the effective diameter of the fully inflated first balloon is uniform along its entire length, because the portion of the first balloon inside the second balloon is of a slightly smaller diameter than the portion outside the second balloon, to accommodate the thickness of the deflated second balloon. In one embodiment, at least about 35% but less than about 80% of the inflatable length of the first balloon is inside the second balloon. In another embodiment, less than about 35% of the inflatable length of the first balloon is inside the second balloon.

On any of the foregoing catheters, a third balloon may be provided proximally of the second balloon. The third balloon is preferably attached to the second balloon in substantially the same manner as the second balloon is attached to the first balloon, either by prolapsing the second or third balloon, bonding the proximal end of the second balloon to the wall of the third balloon, or bonding the distal end of the third balloon to the wall of the second balloon. Where the proximal end of the second balloon is at least partially inside the third balloon, the maximum inflated diameter of that portion of the second balloon may be slightly decresed from that portion of the second balloon outside of the third balloon, preferably by an amount equal to the thicknesses of the third balloon overlying the second balloon when the second balloon is inflated and the third balloon is deflated. In one embodiment of this design, less than about 35% of the inflatable length of the second balloon is inside of the third balloon. Alternatively, in another design, at least about 35% of the inflatable length of the second balloon is inside the third balloon.

In yet another embodiment of the present invention, a third balloon may be provided on top of the distal portion of the second balloon and on top of the proximal portion of the first balloon where the maximum inflated diameter of the third balloon is larger than the maximum inflated diameter of the second balloon, and the proximal end of the third balloon is bonded to the wall of the second balloon and the distal end of the third balloon is bonded to the wall of the first balloon. In this design, spaces conserved because the third balloon "bridges" the gap in between the first balloon and the second balloon, and substantial portions of each of the first balloon and the second balloon are inside of the third balloon.

In all of the embodiments of the present invention, radiopaque markers may be provided on the catheter to mark the longitudinal location of any or all of the balloons on the catheter.

For coronary angioplasty, it is preferred that none of the balloons exceed about 40 mm in length, and most preferably none of the balloons exceed about 30 mm in length. For peripheral angioplasty, it is preferred that none of the balloons exceed about 100 mm in length, and they most preferably do not exceed about 80 mm in length. For coronary angioplasty, it is preferred that the maximum inflated diameter of each of the balloons does not exceed about 4.5 mm. For peripheral angioplasty, it is preferred that the maximum inflated diameter of each of the balloons does not exceed about 15 mm.

Also provided in accordance with the present invention is a surgical procedure for performing vascular balloon angioplasty, comprising the steps of selecting an angioplasty catheter having thereon a first balloon with a first predetermined maximum inflated diameter and a second balloon with a different second maximum inflated diameter, positioning the first balloon inside a first stenosis in a blood vessel and inflating the first balloon to dilate the first stenosis, and positioning the second balloon inside a second stenosis in a blood vessel and inflating the second balloon to dilate the second stenosis. The first balloon should be deflated after dilating the first stenosis and before dilating the second stenosis. The procedure is preferably performed on atherosclerotic stenoses.

The predetermined maximum inflated diameter of the first balloon is preferably approximately equal to the diameter of the native vessel in which the first stenosis is located, and the predetermined maximum inflated diameter of the second balloon is preferably approximately equal to the diameter of the native vessel in which the second stenosis is located. The vessels in which the procedure of the present invention is performed may be coronary arteries.

In accordance with another aspect of this invention, the angioplasty catheter has a third balloon thereon, wherein the third balloon has a maximum inflated diameter different from that of the first balloon and the second balloon, and the method further comprises the steps of positioning the third balloon inside a third stenosis in a blood vessel, and inflating the third balloon to dilate the third stenosis. The third stenosis may advantageously be an atherosclerotic stenosis, and the predetermined maximum inflated diameter of the third balloon is preferably approximately equal to the diameter of the native vessel in which the third stenosis is located.

In accordance with yet another aspect of the surgical procedure of the present invention, there is provided a method for performing balloon angioplasty comprising the steps of selecting an angioplasty catheter having a first balloon with a first predetermined maximum inflated diameter and a second balloon having a different, larger predetermined maximum inflated diameter than the first balloon, wherein the first balloon is located on the catheter distally of the second balloon, positioning the first balloon inside a stenosis inside a blood vessel, inflating the first balloon to dilate the stenosis, advancing the second balloon into the partially dilated stenosis, and inflating the second balloon to further dilate the stenosis. It is preferred that the maximum inflated diameter of the second balloon is approximately equal to the diameter of the native vessel in which the stenosis is located. The vessels may advantageously be coronary arteries.

BRIEF DESCRIPTION OF THE DRAWINGS

FIG. 1 is a perspective view of the distal end of a three-balloon catheter of the present invention, in which the balloons are shown partially cut away.

FIG. 2 is a cross-section of the catheter of FIG. 1, taken along the line 2—2.

FIG. 3 is a cross-section of the catheter of FIG. 1, taken along the line 3—3.

FIG. 4 is a cross-section of the catheter of FIG. 1, taken along the line 4—4.

FIG. 5 is a cross-section of the catheter of FIG. 1, taken along the line 5—5.

FIG. 6 is a detailed view of the central attachment site of a catheter, showing the balloons in cross-section, illustrating separate tandem bonding.

FIG. 7 is a close-up view of the central attachment site of a catheter, with the balloon shown in cross-section, illustrating prolapse bonding.

FIG. 8 is a close-up view of the central attachment site of a catheter, illustrating the method of making an overlap joint, showing the balloons and a die in cross-section.

FIG. 12 is a schematic representation of a tandem double balloon catheter with contiguous tandem bonding and an axial torque guidewire.

FIG. 13 is a schematic representation of a tandem double balloon catheter utilizing prolapse bonding for use with a steerable guidewire.

FIG. 14 is a schematic representation of a tandem double balloon catheter utilizing overlap-proximal bonding for use with a steerable guidewire.

FIG. 15 is a schematic representation of a tandem double balloon catheter with overlap-proximal bonding and an axial torque guidewire.

FIG. 16 is a schematic representation of a tandem double balloon catheter with overlap-distal bonding for use with a steerable guidewire.

FIG. 17 is a schematic representation of a tandem double balloon catheter with overlap-distal bonding and an axial torque guidewire.

FIG. 18 is a schematic representation of a semi-concentric double balloon catheter with overlap-distal bonding for use with a steerable guidewire.

FIG. 19 is a schematic representation of a semi-concentric double balloon catheter with overlap-distal bonding and an axial torque guidewire.

FIG. 20 is a schematic representation of a tandem double balloon catheter with internal partition bonding for use with a steerable guidewire.

FIG. 21 is a schematic representation of a tandem triple balloon catheter with overlap-proximal bonding for use with a steerable guidewire.

FIG. 22 is a schematic representation of a tandem triple balloon catheter with overlap-proximal bonding and an axial torque guidewire.

FIG. 23 is a schematic representation of a tandem triple balloon catheter with overlap-distal bonding for use with a steerable guidewire.

FIG. 24 is a schematic representation of a tandem triple balloon catheter with overlap-distal bonding and an axial torque guidewire.

FIG. 25 is a schematic representation of a tandem triple balloon catheter with overlap bridge bonding for use with a steerable guidewire.

DETAILED DESCRIPTION OF THE INVENTION

I. CATHETER DESIGN

Figure 9:
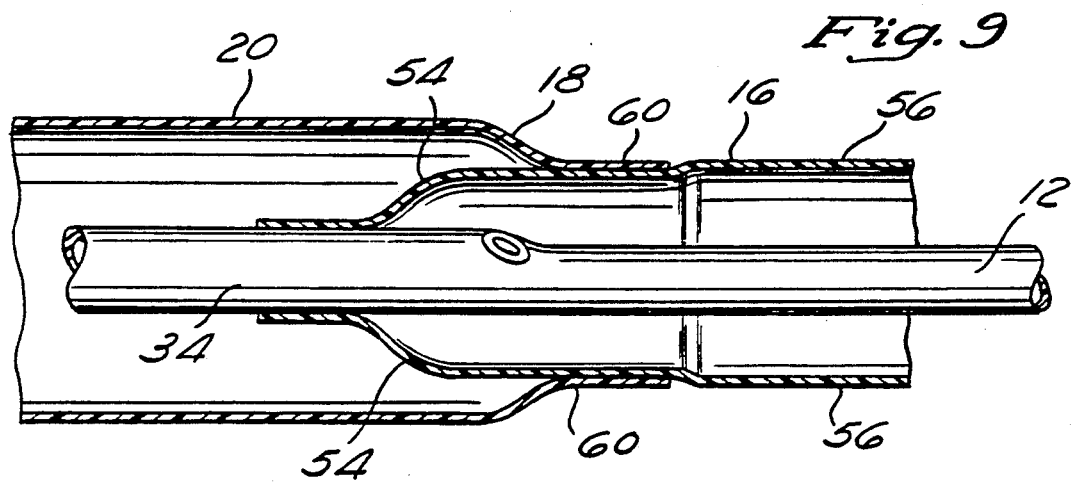
FIG. 9 is a close-up view of the central attachment site of a catheter, with the balloons in cross-section, illustrating the construction of an overlap-distal joint.

The catheters of the present invention may be fabricated from conventional commercially available polymers, but may also utilize improved materials in the future as they become available. The balloon segments of the present invention may be shaped or blown using well known hot water bath, heat torch, or thermal oven methods. The balloon joint bonding processes that may be used include heat bonding, vulcanization bonding, solvent bonding, ultrasonic welding, laser bonding, and glue bonding.

In order to achieve the objectives of the present invention, a number of different embodiments of the angioplasty balloon catheter have been provided. These different balloon models can be classified according to the architectural embodiment and can be subclassified according to their functional characteristics and according to the fabrication techniques used, and especially balloon attachment techniques and balloon geometry.

The following is a summary of different embodiments and permutations of the present invention:
(1) Models of Balloon Design
  (a) Tandem Double Balloons
  (b) Semi-Concentric Double Balloons
  (c) Tandem Triple Balloons
(2) Functional Types of Balloons Catheters
  (a) Steerable Guidewire type
  (b) Bypass Sidehole type
  (c) Axial Torque type
(3) Variations of Balloon Joint Bonding
  (a) Contiguous tandem bonding
  (b) Prolapse tandem bonding
  (c) Overlap Tandem bonding
    (i) Proximal overlap
    (ii) Distal overlap
  (d) Overlap-bridge
  (e) Overlap-partition.

Many features common to all the balloon designs of the present invention are illustrated in FIG. 1. With reference to FIG. 1, the catheter 10 of the present invention is provided with a catheter shaft 12 having a distal end 14 and a proximal end (not shown) opposite the distal end.

A first balloon 16 is provided near the distal end 14 of the catheter shaft 12. The first balloon 16 may be formed of polyvinylchloride, polyethylene, Mylar brand polyester material (made by duPont), or other suitable film-forming material capable of withstanding pressures of 100 psi, preferably 150 psi or even 200 psi, without bursting or significantly stretching, when formed into a thin-walled angioplasty balloon. Mylar is particularly preferred. Generally, the thickness of the walls 18 of the balloons will be between about 0.01 mm and 0.10 mm. This thickness is greatly exaggerated in the Figures for purposes of illustration only. The balloon 16 may be attached to the catheter shaft 12 using any of the well known connection techniques, including solvent bonding, adhesive bonding, heat-shrink bonding, thermal welding and so on. The first balloon 16 may be heat formed or blown to the desired shape and configuration. The first balloon is preferably generally cylindrical, and may be tapered at the proximal and distal ends.

A second balloon 20 is provided on the catheter shaft 12 proximally of the first balloon 11 and adjacent to the first balloon 16. As illustrated in FIG. 1, the inflated diameter of the first balloon 16 is less than the inflated diameter of the second balloon 20.

In addition to the first and second balloons 16, 20, a third balloon 21 may be provided adjacent to the proximal end of the second balloon 20. The third balloon is constructed of substantially the same material in substantially the same manner as the first balloon 16 and the second balloon 20.

The catheter shaft 12 is provided with a central lumen 22, a first lumen 24, and a second lumen 26. The central lumen 22 extends longitudinally through the catheter shaft 12 and terminates at the distal end 14 of the catheter 10. The first lumen 24 extends through the catheter shaft 12 and terminates inside the first balloon 16, permitting the first balloon 16 to be individually inflated and deflated by the introduction and removal of fluid through the first lumen 24 as indicated by the arrow 25. Similarly, the second lumen 26 terminates inside the second balloon 20, permitting the second balloon 20 to be separately inflated and deflated by introduction of and removal of fluid through the second lumen 26 as indicated by the arrows 27.

A third lumen 28 is provided in the catheter shaft 12 in fluid communication with the interior of the third balloon 21, thereby permitting the third balloon 21 to be inflated and deflated by introducing fluid into and removing fluid from the interior of the third balloon 21 via the third lumen 28 as indicated by arrow 29.

Radiopaque markers 32 are provided inside each of the balloons on the catheter shaft 12. These radiopaque markers 32, which may advantageously be made of metal or other radiopaque material, are preferably longitudinally located on the catheter shaft in the center of each of the balloons 16, 20, 21. In this way, the exact placement of the balloons can be ascertained through fluoroscopy during angioplasty procedure.

The catheter shaft may be constructed in any desired way to provide the requisite number of lumens terminating inside the desired balloons. The catheter 10 is shown in several cross sections in FIGS. 2, 3, 4, and 5. In FIG. 2, a cross section of the catheter shaft 12 taken proximally of all of the balloons 16, 20, 21 along the line 2—2, it can be seen that the catheter shaft 12 (which may be made of any suitable medical plastic) has a central lumen 22, a first lumen 24, a second lumen 26, and a third lumen 28 running therethrough. Note that, while the central lumen 22 is larger than the numbered lumens 24, 26, 28, the central lumen need not be actually centrally located in the catheter shaft 12.

With reference now to FIG. 3, this is a cross-section of the catheter 10 through the third balloon 21 along the line 3—3. Note that the catheter shaft 12 now has a central lumen 22, a first lumen 24, and a second lumen 26. There is no longer any third lumen 28, this lumen having terminated inside the third balloon 21. The third balloon 21 is shown fully inflated, although it will, of course, ordinarily be deflated and collapsed against the catheter shaft 12.

FIG. 4 illustrates the balloon construction in a cross-section taken along the line 4—4 through the second balloon 20. Note that the catheter shaft 12 now has only the central lumen 22 and the first lumen 24, the second lumen 26 having terminated inside the second balloon 20. The second balloon 20 concentrically surrounds the catheter shaft 12. In FIG. 4, the second balloon 20 is illustrated in fully inflated form. However, the second balloon 20 will ordinarily be fully deflated and collapsed against the catheter shaft 12.

FIG. 5 is a cross-section taken along the line 5—5 through the first balloon 16. Note that the catheter shaft 12 now has only a single lumen, the central lumen 22 through which a steerable guidewire may be inserted. The first balloon 10 surrouds the catheter shaft 12 concentrically and, like the other balloons 20, 21, is coaxial with the catheter shaft 12.

A number of possibilities exist for connecting the balloons to the shaft and/or to adjacent balloons. When balloons are mounted in simple tandem, that is, one after the other on the shaft, there is a "dead space" between the balloons. Various bonding techniques are possible to eliminate this dead space and, thus, to permit more balloons in a smaller amount of space than was heretofore possible.

A simple tandem bonding joint between two balloons is illustrated in FIG. 6. In this drawing, a first balloon 16 and a second balloon 20 are provided on the catheter shaft 12. Between the balloons is a central attachment site 34 to which the proximal end of the first balloon 16 and the distal end of the second balloon 20 are attached. In FIG. 6, the first balloon 16 and the second balloon 20 are made from a single, continuous piece of balloon material. When the balloons 16, 20 are blown from this single piece of material, and are shaped to have the desired diameters, a narrow waist 36 is formed in the balloon material having a lesser diameter than either of the ballons 16, 20. This narrow waist 36 is bonded to the catheter shaft 12 at the central attachment site 34. This construction is referred to as contiguous tandem construction because the balloons 16, 20 are formed from a single, continuous piece of balloon material and they are mounted in tandem on the catheter shaft.

Of course, it is possible to form the balloons 16, 20 of separate pieces of balloon material and to then mount them on the catheter shaft, one next to the other. This is referred to as separate tandem bonding.

An alternative bonding technique is illustrated in FIG. 7. This technique is referred to as prolapse tandem bonding. With prolapse bonding, the effective length of the catheter 10 occupied by the balloons 16, 20 may be shortened by prolapsing one of the balloons over the attachment site 34. Either of the balloons 16, 20 can be prolapsed partially or fully over the bonding site 34, although it is preferred to prolapse the first balloon 16 over the central attachment site 34. Thus, in FIG. 7, the distal end of the second balloon 20 and the proximal end of the first balloon 16 are attached to the catheter shaft 12 at the central attachment site 34. The proximal end of the first balloon 16 is then folded proximally (prolapsed) back over at least a portion of the central attachment site 34. It is preferred that the first balloon 16 is prolapsed over substantially all of the central attachment site 34 so that the prolapsed portion 40 of the first balloon 16 is directly adjacent to or even in contact with the second balloon 20. This prolapse design permits the elimination of the dead space of the central attachment site 34, providing a shorter, more easily manipulated balloon portion of the catheter 10. This shortened arrangement is advantageous in negotiating tight turns during the insertion and positioning of the catheter. This shortened arrangement also minimizes the extent of the occupation of the distal artery lumen with the unused distal balloon when the proximal balloon is in use. The prolapsed portion 40 is a part of the inflatable portion of the first balloon 16 and is located over the central attachment site 34 and over the point where the proximal end of the first balloon 16 is connected to the catheter shaft 12.

One suitable fabrication technique for the prolapse design is to bond the second balloon 20 to the catheter shaft 12 through any conventional bonding technique, such as heat shrink bonding, solvent welding, adhesive bonding, ultrasonic bonding, heat bonding, or other suitable technique. The proximal end of the first balloon 16 is also bonded to the central attachment site 42 on the catheter shaft 12. The first balloon is then prolapsed into the desired position, and then the prolapsed portion 40 of the first balloon 16 is bonded to the catheter shaft 12 in a suitable way, such as with adhesive 42 or with a solvent. In one suitable technique, the second balloon 20 and the first balloon 16 are inflated with positive pressure, (e.g., 100–120 psi) and the prolapsed portion 40 of the first balloon 16, which is in contact with the central attachment site, and optionally, in contact with the second balloon 20, is bonded thereto with solvent or adhesive welding. This bonding technique ensures that the first balloon 16 maintains its prolapsed position and will prevent forward and backward "rolling" during catheter movements and balloon inflation.

Yet another bonding technique that may be used to attach the balloons of the present invention is illustrated in FIG. 8. This technique is referred to as overlap proximal bonding. As illustrated in FIG. 8, the distal end of the second balloon 20 is attached to the central attachment site 34 as has been previously described. The second balloon 20, at its distal end, preferably has a tapered portion 44 at its distal end where the second balloon 20 tapers down from its maximum inflated diameter to the diameter of the shaft 12. The proximal end of the first balloon 16 is bonded, not to the catheter shaft 12, but to the wall 18 of the second balloon 20 proximally of the point where the distal end of the second balloon 20 is attached to the central attachment site 34, preferably on the tapered portion 44 of the second balloon 20. In this way, a part of the inflatable portion of the first balloon 16 is over the central attachment site 34.

In order to maintain an ideal profile for the first and second balloons 16, 20, when inflated, it is preferred that the inflated diameters of the proximal end of the first balloon 16 and the part of the tapered portion 44 of the second balloon 20 to which it is bonded be substantially the same. Of course, the same result can be achieved by bonding the distal end of the second balloon 20 to the wall of the proximal end of the first balloon 16 distally of the point where the first balloon 16 is attached to the central attachment site 34.

The fabrication method for forming the overlap joint between the first balloon 16 and the tapered portion 44 of the second balloon 20 may be any suitable technique, such as solvent bonding, adhesive bonding, vulcanization, or ultrasonic welding. In order to create the overlap balloon joint, the proximal end of the first balloon 16 which is to be bonded to the tapered portion 44 of the second balloon 20 preferably has a flared end 46 to fit the taper and diameter of the tapered portion 44. Once the first balloon 16 has been properly placed on the tapered portion 44 of the second balloon 20, and adhesive 42 or solvent has been applied to the joint, the catheter is preferably inserted into a die 50 having a cavity 52 that matches the contours of the inflated first balloon 16 and the inflated second balloon 20. The second balloon may then be fully inflated inside the die, pressing the overlap joint on the tapered portion 44 against the inside of the die until the joint has cured.

Still another alternative balloon joint design is illustrated in FIG. 9. This design is referred to as semi-concentric bonding, because one balloon is actually partially inside another balloon. With reference to FIG. 9, the proximal end of the first balloon 16 is attached to the catheter shaft 12 at the central attachment site 34. The second balloon 20 overlaps the central attachment site 34, and the distal end of the second balloon 20 is bonded to the wall of the first balloon 16 distally of the proximal end of the first balloon 16 and the central attachment site 34. Thus, at least a portion 54 of the inflatable length of the first balloon 16 is inside the second balloon 20. This inside portion 54 may be relatively short, or it may comprise at least 10%, preferably at least 20%, and most preferably at least 35% of the inflatable length of the first balloon 16. The inside portion 54 should comprise less than 95% of the inflatable length of the first balloon 16, preferably less than 90% of the inflatable length of the first balloon 16, and most preferably less than 80% of the inflatable length of the first balloon 16.

In accordance with one preferred embodiment of the present invention, the inside portion 54 of the first balloon 16 is of a slightly smaller diameter than the maximum inflated diameter of the outside portion 56 of the first balloon 16. The difference between the diameter of the inside portion 54 and the outside portion 56 is preferably approximately equal to the thickness of the balloon 20 overlying the inside portion 54 when the first balloon 16 is fully inflated and the second balloon 20 is deflated. In this way, the overlap joint 60 presents a smooth profile in use and the effective working diameter of the first balloon 16 remains constant over its entire length. That is because the effective working diameter of the inside portion 54 of the inflated first balloon 16 includes the deflated thicknesses of the wall 18 of the second balloon 20 overlying the inside portion 54.

Figure 10:
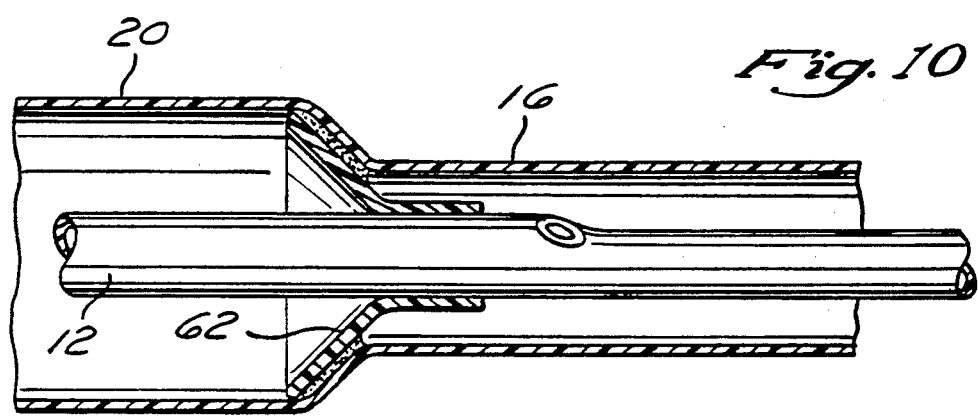
FIG. 10 is a close-up view of the central attachment site of a catheter, with the balloons in cross-section, illustrating an internal partition joint.

Another alternative balloon construction method is the internal partition method. This design is illustrated in FIG. 10. The first balloon 16 and the second balloon 20 are blown from a single tube of balloon material. The material is formed to taper gently over the central attachment site 34 from the maximum inflated diameter of the first balloon 16 out to the maximum inflated diameter of the second balloon 20. An internal partition 62 of balloon material is provided inside of the tube comprising the first balloon 16 and the second balloon 20. This partition separates the first and second balloons 16, 20. The partition is preferably frusto-conical in shape, with the narrow, distal end thereof bonded to the catheter shaft 12 and the wider, proximal end thereof bonded to the inside of the tube forming balloons 16, 20, and is positioned between the balloons 16, 20.

Figure 11:
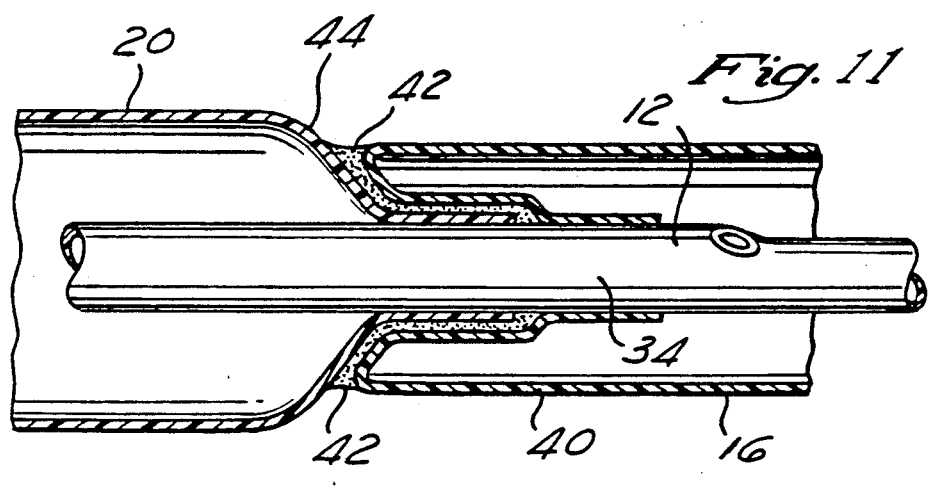
FIG. 11 is a close-up view of the central attachment site of a catheter according to the present invention, with the balloons in cross-section, illustrating a different type of prolapse joint.

An alternative type of prolapsed joint is illustrated in FIG. 11. This prolapse joint is very similar to the joint illustrated in FIG. 7. Unlike the design of FIG. 7, the proximal end of the first balloon 16 is folded back on itself only once (not twice). In constructing this prolapsed joint, the first balloon 16 is positioned on the catheter shaft 12 with the proximal end of the first balloon 16 on the central attachment site 34 and what is to be the distal end of the first balloon 16 located proximally (not distally) of the central attachment site 34. The proximal end of the first balloon 16 is then bonded to the central attachment site 34, after which the first balloon 16 is folded back over itself until the distal end of the first balloon 16 is distal of the central attachment site 34. Thus, the first balloon 16 is literally turned inside out. The distal end of the second balloon 20 is then attached to the central attachment site 34, the prolapsed portion 40 of the first balloon 16 is bonded to the central attachment site and, preferably, the tapered portion 44 of the second balloon 20, using adhesive 42 or an appropriate solvent.

Several specific embodiments of the balloon catheter 10 of the present invention will be described hereinafter in greater detail in connection with schematic drawings of the catheter construction. To the extent that the elements of the catheter 10 remain the same from embodiment to embodiment, the same reference numerals will be used.

A. Tandem Double Balloons

1. Axial Torque Type

This particular balloon design utilizes the tandem joint illustrated in FIG. 6 with an axial torque guidewire. The smaller distal balloon is bonded to the axial torque guidewire and the larger, proximal balloon is bonded to the catheter shaft.

Thus, with reference to FIG. 12, a tandem double balloon of the axial torque type is illustrated in schematic fashion. The catheter 10 has a catheter shaft 12 on which are mounted a first balloon 16 and a second balloon 20. The first balloon 16 is smaller than the second balloon 20 in diameter, and is located distally of the second balloon 20.

The catheter shaft 12 is provided with multiple longitudinal lumens or passageways therethrough. These lumens are schematically illustrated in FIG. 12 as twodimensional paths between solid lines. Thus, on the proximal side of the balloons 16, 20, the catheter shaft 12 includes two lumens, the central lumen 22 and the second lumen 26. The solid line inside the central lumen 22 represents the axial torque guidewire 64 extending through the central lumen 22 and out of the distal end of the catheter shaft 12.

The second balloon 20 is attached to the catheter shaft 12 at both its proximal end and its distal end. The second lumen 26 terminates inside the second balloon 20, providing for independent inflation and deflation of the second balloon 20 by introducing fluid into and removing fluid from the second balloon 20 through the second lumen 26.

The proximal end of the first balloon 16 is attached to the distal end of the catheter shaft 12, and the distal end of the first balloon 16 is attached to the axial torque guidewire 64. Note that, in this design, there is no first lumen 24, its function being fulfilled by the central lumen 22 through which the axial torque guidewire 64 extends. Thus, the central lumen 22 is large enough to accommodate not only the axial torque guidewire 64 but also to permit introduction of fluid into the first balloon 16 and removal of fluid from the first balloon 16 to inflate and deflate the first balloon 16.

The axial torque guidewire 64 is flexible and shapable. It comprises a tapered steel mandrel running from the proximal end of the catheter 10 (not shown) and out of the distal end 14 of the catheter 10, terminating in a shapable distal guidewire tip 66 extending out of the distal end of the first balloon 16. The shapable tip 66 extending distally out of the first balloon 16 is preferably 0.012 inches to 0.014 inches in diameter, and the remainder of the axial torque guidewire 64 through the catheter shaft 12 may advantageously be 0.018 inches to 0.020 inches in diameter.

In use, torque may be applied to the axial torque guidewire 64 at the proximal end of the catheter 10. This torque is transmitted by the steel mandrel portion of the axial torque guidewire 64 to the shapable guidewire tip 66 and is used to steer the guidewire tip to subselect the desired vessel branches during the angioplasty procedure.

The first balloon 16 and the second balloon 20 may be formed from a single, continuous piece of balloon material, having a narrow waist 36 bonded to the central attachment site 34, as shown in FIG. 6. Alternatively, the two balloons 16, 20 may be formed of separate pieces of material.

In a preferred fabrication procedure, after heating the balloon material to the softening temperature thereof and blowing the balloons 16, 20 to the desired shape inside an appropriately-sized die, the balloons 16, 20 are then bonded to the catheter shaft 12 and the axial torque guidewire 64 using any suitable technique.

The fabrication method for the balloons may be the same as the conventional currently-available fabrication techniques for single balloon catheters. See, e.g., U.S. Pat. Nos. 4,195,637 and 4,323,071.

A typical catheter 10 could have a first balloon 16 that is 2.0 mm in diameter and 15 mm in length, and a second balloon 20 that is 2.5 mm in diameter and 20 mm in length. However, the balloons 16, 20 can be made in any variation and combination of sizes, with balloon diameters for coronary angioplasty of from about 1.0 mm to about 5.0 mm and lengths from about 7 mm to about 40 mm, respectively. Thus, the diameter of the first balloon 16 may be 1.0 mm, 1.5 mm, 2.0 mm, 2.5 mm, 3.0 mm, or 3.5 mm, and the diameter of the second balloon 20 may be 1.5 mm, 2.0 mm, 2.5 mm, 3.0 mm, 3.5 mm, 4.0 mm, or 5.0 mm (provided that the second balloon 20 has a greater diameter than the first balloon 16). Similarly, the length of both the first balloon 16 and the second balloon 20 may be 7 mm, 10 mm, 12 mm, 15 mm, 20 mm, 25 mm, 30 mm, 35 mm, or 40 mm. For peripheral and valvular angioplasty, significantly larger balloon sizes are appropriate, with balloon lengths up to about 80 mm or 100 mm and diameters up to about 10 mm, or, conceivably, 15 mm.

B. Tandem Double Balloons/Prolapse Tandem

1. Steerable Guidewire Type

In accordance with one advantageous embodiment of the tandem balloon design, the effective length of the catheter occupied by the two balloons may be shortened by prolapsing one of the balloons, as discussed in connection with FIG. 7. As shown schematically in FIG. 13, the first balloon 16 and the second balloon 20 are mounted on the catheter shaft 12 in the same way as discussed in connection with FIG. 12. The proximal end of the first balloon 16 and the distal end of the second balloon 20 are attached to the catheter shaft 12 at a point denominated as the central attachment site 34. The proximal end of the first balloon 16 is then folded proximally (prolapsed) back over at least a portion of the central attachment site 34, as shown in more detail in FIG. 7. Alternatively, instead of the prolapse construction shown in FIG. 7 (a double-fold prolapse design), the catheter may utilize the prolapse construction shown in FIG. 11 (a single-fold prolapse design). In either event, it is preferred that the first balloon 16 is prolapsed over substantially all of the central attachment site 34 so that the prolapsed portion 40 is directly adjacent to, or even in contact with, the second balloon 20. This prolapse design eliminates the dead space of the central attachment site 34, providing a shorter, more easily manipulated and safer balloon portion of the catheter 10.

This balloon design includes a central lumen 22 in the catheter shaft 12. The catheter shaft 12 and the central lumen 22 extend completely through both the first balloon 16 and the second balloon 20, and extend distally from the first balloon 16. The central lumen 22 is large enough to accommodate a steerable guidewire (not shown) of conventional design. Unlike the axial torque guidewire discussed in connection with FIG. 12, the steerable guidewire is not connected to the distal portion of the catheter 10, and can freely rotate and slide inside the central lumen 22. Steering of the catheter 10 by use of the steerable guidewire is accomplished in the conventional manner by rotating the guidewire.

The dimensions of the central lumen are sufficient to accommodate a 0.014 inch steerable guidewire and, at the same time, to permit monitoring of the distal pressure through the central lumen 22.

The outside diameter of the catheter shaft 12 should not be larger than about size French 4.5 or 4.7.

2. Bypass Sidehole

In one preferred embodiment of the design illustrated in FIG. 13, the catheter may be provided with proximal holes 70 on the proximal side of the second balloon 20 and with distal holes 72 in the catheter shaft 12 distally of the first balloon 16. These holes 70, 72 are shown schematically in FIG. 13, and communicate with a lumen that is not used for inflating or deflating the balloons 16, 20. Although a special lumen may be provided with which the holes 70, 72 communicate, the holes 70, 72 preferably are connected only to the central lumen 22 and do not interrupt or connect with any other lumen. Thus, these holes provide a means for permitting the flow of blood through the catheter shaft past the balloons 16, 20. The provision of the holes 70, 72 to permit blood to bypass the balloons 16, 20 is important in angioplasty procedures in which it is desirable to prevent occlusion of the blood vessel during the positioning, inflation, deflation, and removal of the balloons. Thus, even when one of the balloons 16, 20 is inflated, occluding the vessel, blood can flow through the proximal holes 70, through the central lumen 22, and out of the distal holes 72 and out of the end 14 of the catheter 10. Because of the holes 70, 72, distal pressure monitoring through the central lumen is not possible, although a separate lumen could be provided for that purpose. Nevertheless, a conventional steerable guidewire may be used with the bypass sidehole type catheter.

It is preferred that the proximal holes 70 are located within about one inch of the proximal end of the second balloon 20. Three to five proximal holes may advantageously be used. The distal holes 72 may advantageously be located between the distal end 14 of the catheter 10 and the distal joint where the first balloon 16 is joined at its distal end to the catheter shaft 12. Two distal holes 72 will ordinarily be sufficient.

3. Axial Torque Type

The axial torque type prolapse tandem double balloon design is substantially identical to the design illustrated in FIG. 11, except that the first balloon 16 and the second balloon 20 are joined to the central attachment site 34 in a prolapsed manner, as illustrated in connection with FIG. 7. The prolapsed joint of. FIG. 7 is, thus, substituted for the separate tandem joint in the design illustrated in FIG. 12.

The axial torque type tandem double balloon catheter with prolapse bonding has the advantage of a much smaller collapsed first balloon profile. Moreover, because the catheter shaft 12 does not extend through the first balloon 16, the distal end of the catheter 10 is more flexible than the steerable guidewire-type catheter. The low profile of the distal first balloon 16 is particularly advantageous for penetrating and dilating or predilating tightly constricted stenoses.

C. Tandem Double Balloon/Overlap-Proximal

1. Steerable Guidewire Type

Fig. 14 schematically illustrates a tandem double balloon catheter with proximal overlap bonding between the first balloon 16 and the second balloon 20. In this design, a first balloon 16 is located at the distal end of the catheter shaft 12. A second balloon 20 is also provided on the catheter shaft 12 just proximally of the first balloon 16. A central lumen 22 extends through the catheter shaft 12 and through both the first balloon 16 and the second balloon 20, terminating in an opening at the distal end 14 of the catheter 10. A first lumen 24 communicates with the interior of the first balloon 16, which can be inflated and deflated separately by introducing fluid into and removing fluid from the interior of the first balloon 16 through the first lumen 24. Similarly, a second lumen 26 communicates with the interior of the second balloon 20, permitting separate inflation and deflation of the second balloon 20 in the same manner.

The proximal end of the second balloon 20 is attached to the catheter shaft 12, and the distal end of the second balloon 20 is attached to the catheter shaft 12 at the central attachment site 34. The distal end of the first balloon 16 is attached to the catheter shaft 12, and the proximal end of the first balloon is attached to the wall of the second balloon proximally of the attachment site 34 on the catheter shaft 12. This proximal overlap joint is illustrated more fully in FIG. 8. Thus, it can be seen in FIG. 14 that a part of the inflatable portion of the first balloon 16 is over the central attachment site 34.

As discussed more fully in connection with FIG. 8, the flared end 46 of the first balloon 16 is attached to the tapered portion 44 at the distal end of the second balloon 20 where the second balloon 20 tapers from its maximum inflated diameter down to the diameter of the catheter shaft 12.

This design has the advantage of significantly shortening the overall catheter length by placing the central attachment site 34 inside of the first balloon 16.

The central lumen 22 through the catheter shaft 12 is appropriately sized to receive a steerable guidewire of the type previously discussed.

2. Bypass Sidehole Type

In one preferred embodiment of the design illustrated in FIG. 14, the catheter may be provided with proximal holes 70 on the proximal side of the second balloon 20 and with distal holes 72 on the distal side of the first balloon 16. As discussed in connection with FIG. 13, these holes 70, 72 permit blood to bypass the balloons 16, 20 through the central lumen 22 to perfuse the distal myocardial segment.

3. Axial Torque Type

A different embodiment of the overlap-proximal tandem double balloon is illustrated in FIG. 15. In this design, as in FIG. 14, the proximal end of the first balloon 16 is bonded to the wall 18 of the second balloon 20. The distal end of the second balloon 20 is connected to the catheter shaft 12 at the distal end 14 of the catheter shaft 12 on the central attachment site 34. The proximal end of the first balloon 16 is preferably flared and may advantageously be joined to the tapered portion 44 of the second balloon where the second balloon tapers at its distal end down from its maximum inflated diameter to the diameter of the catheter shaft 12. It should be noted that the central attachment site 34 is inside the inflatable portion of the first balloon 16.

As in FIG. 12, an axial torque guidewire 64 extends through the central lumen 22 and through the second balloon 20 and the first balloon 16. The distal end of the axial torque guidewire 64 comprises a shapable guidewire tip 66, substantially as described in connection with FIG. 12. The distal end of the first balloon 16 is bonded to the axial torque guidewire 64. Radiopaque markers 32 are provided in the center of each of the balloon 16, 20.

A first lumen 24 is not needed in this design because the central lumen 22 terminates inside the first balloon 16 and serves the function of both carrying the axial torque guidewire 64 and permitting the separate inflation and deflation of the first balloon 16. A second lumen 26 terminates inside the second balloon 20 for separate inflation and deflation of the second balloon 20.

One novel fabrication technique for this particular balloon design involves blowing the balloons 16, 20 after they are attached to the catheter shaft 12. The distal end of the polymer tube from which the second balloon 1 is to be made is bonded to the catheter shaft 12 at the central attachment site 34. Next, the unblown polymer tube that will be formed into the first balloon 16 is flared open at its proximal end and is placed over the distal end 14 of the catheter shaft 12 and over the distal end of the tube that will form the second balloon 20, preferably 2-3 mm away from the central attachment site 34.

If solvent or adhesive welding is to be used, the flared end of the tube to be formed into the first balloon 16 is bonded to the tube that will form the second balloon 20. If heat bonding is desired, on the other hand, a hollow mandrel of suitable heat resistant material should be placed inside the tubes of balloon material on the catheter shaft 12 from the proximal end of the shaft 12. With this heat protective material in place directly underneath what is to become the overlap joint between the first balloon 16 and the second balloon 20, heat may be applied to the joint to bond the two layers of balloon material. The heat-resistant tube is then removed from the catheter shaft 12, the balloon material is bonded to the catheter shaft 12 at the proximal end of the second balloon 20 and the distal end of the first balloon 16, and then the balloon material is heated and blown in a die having an inner chamber matching the desired contours of the finished first and second balloons 16, 20.

D. Tandem Double Balloon/Overlap-Distal

1. Steerable Guidewire Type

FIG. 16 schematically illustrates a somewhat different balloon design in which both the proximal and distal ends of the first balloon 16 are bonded to the catheter shaft 12. The proximal end of the first balloon 16 is attached to the catheter shaft at the central attachment site 34. The proximal end of the second balloon 20 is attached to the catheter shaft 12, and the distal end of the second balloon 20 is attached to the wall of the first balloon 16 distally of the central attachment site 34 to form an overlap joint 60. This joint construction is more fully illustrated in FIG. 9.

The central attachment site 34 is inside the second balloon 20, as is the inside portion 54 of the first balloon 16. In the embodiment illustrated in FIG. 16, less than 35% of the total inflatable length of the first balloon 16 is inside the second balloon 20.

A central lumen 22 for receiving a steerable guidewire extends through the length of the catheter shaft 12 and through both the first balloon 16 and the second balloon 20. A first lumen 24 communicates with the interior of the first balloon 16 for inflation and deflation of that balloon, and a second lumen 26 communicates with the interior of the second balloon 20 for separate inflation and deflation of that balloon.

As with the overlap-proximal joint previously discussed, the overlap-distal joint illustrated in FIGS. 9 and 16 may advantageously be formed by bonding together the two pieces of balloon material from which the first balloon and second balloon are to be formed prior to blowing those balloons, similar to the technique described in connection with the overlap-proximal joint. The first balloon 16 and the second balloon 20 are preferably separately blown in appropriately-sized dies, blowing first the smaller, first balloon 16 and then the larger, second balloon 20.

In one preferred embodiment of the overlap-distal balloon, the inside portion 54 of the first balloon 16 has a smaller maximum inflated diameter than does the outside portion 56 of the first balloon 16. When the first balloon 16 is in use in vivo, it is desirable that the inflated first balloon 16 present a substantially uniform diameter along its length. Because only one balloon is inflated at a time, the second balloon 20 on top of the inside portion 54 of the first balloon 16 will be deflated. Thus, it is desirable to provide the inside portion 54 of the first balloon 16 with a diameter that is less than the maximum inflated diameter of the outside portion 56 by a factor approximately equal to the thicknesses of the deflated second balloon 20 overlying the first balloon 16. This decreased thickness is automatically provided when the balloons are blown as described above, with the second balloon 20 already bonded to the first balloon 16.

2. Bypass Sidehole Type

In the same manner as discussed in connection with FIGS. 13 and 14, the balloon design of FIG. 16 may optionally be provided with proximal holes 70 in the catheter shaft 12 proximally of the second balloon 20 and with distal holes 72 on the distal end 14 of the catheter shaft 12 distally of the first balloon 16. These proximal and distal holes 70, 72 may communicate with the central lumen 22, providing a means for blood to flow through the catheter shaft 12 from the proximal side of the balloons 16, 20 to the distal side of the balloons 16, 20, thereby perfusing the distal myocardial segment during balloon inflation.

3. Axial Torque Type

FIG. 17 schematically illustrates an overlap-distal tandem double balloon catheter having the same overlapping balloon design shown in FIG. 16 and discussed in connection therewith. However, unlike FIG. 16, the axial torque type balloon catheter illustrated in FIG. 17 has the steel mandrel of an axial torque guidewire 64 extending through the central lumen 22 and through the first balloon 16 and the second balloon 20. The distal end of the first balloon 16 is bonded directly to the axial torque guidewire 64, in the same way as was discussed in connection with FIGS. 12 and 15. A first lumen 24 is not provided in this design, because the distal end of the central lumen 22 terminates inside the first balloon 16 and serves the function of introducing a fluid into and removing of fluid from the first balloon 16 for inflation and deflation thereof. A second lumen 26 terminates inside the second balloon 20 for separate inflation and deflation of that balloon.

E. Semi-Concentric Double Balloons/Overlap-Distal

1. Steerable Guidewire Type

FIG. 18 is a schematic illustration of a variation of the balloon design illustrated in FIG. 16. Thus, as in FIG. 16, the proximal end of the first balloon 16 is attached to the central attachment site 34 and the distal end of the first balloon 16 is attached to the catheter shaft 12. The proximal end of the second balloon 20 is attached to the catheter shaft 12, and the distal end of the second balloon 20 is attached to the wall of the first balloon 16 distally of the central attachment site 34. This design differs from the design in FIG. 16 in that the inside portion 54 of the first balloon 16 inside the second balloon 20 comprises at least 35% of the inflatable length of the first balloon 16. A central lumen 22 for receiving a steerable guidewire is provided, as are a first lumen 24 for inflation and deflation of the first balloon 16 and a second lumen 26 for separate inflation and deflation of the second balloon 20.

2. Bypass Sidehole Type

As discussed in connection with FIGS. 13, 14, and 16, proximal holes 70 on the proximal side of the second balloon 20 and distal sideholes 72 on the distal side of the first balloon 16 may be provided in the catheter shaft 12 in communication with the central lumen 22 to provide a means for blood to bypass the balloons 16, 20 during balloon inflation.

3. Axial Torque Type

The semi-concentric double balloon catheter illustrated in FIG. 19 is similar to the steerable guidewire design illustrated in FIG. 18 in that at least 35% of the inflatable length of the first balloon 16 is inside the second balloon 20, as is the central attachment site 34 to which the proximal end of the first balloon 16 is bonded. However, as in FIGS. 12, 15, and 17, an axial torque guidewire 64 extends through the central lumen 22 and out through the distal end of the first balloon 16. The distal end of the first balloon 16 is bonded to the axial torque guidewire 64. No separate first lumen 24 is provided, that function being fulfilled by the central lumen 22. A second lumen 26 is provided in the catheter shaft 12 for separate inflation and deflation of the second balloon 20.

F. Tandem Double Balloon/Internal Partition

The internal partition joint illustrated in detail in FIG. 10 may be provided in a single tube of balloon material to provide a tandem double balloon catheter as illustrated in FIG. 20. In this design, the first balloon 16 and the second balloon 20 are formed of a single tube of balloon material which is attached at its proximal and distal ends to the catheter shaft 12. Approximately 45% of the length of the tube of balloon material has a first predetermined maximum inflated diameter, and approximately 55% of the tube of balloon material has a second, larger predetermined maximum inflated diameter, thereby forming the first balloon 16 and the second balloon 20. The first balloon 16 and the second balloon 20 are separated by an internal partition 62 which is bonded to the inside wall of the second balloon 20 at the distal end of the second balloon 20 and is bonded to the catheter shaft 12, thus effectively separating the interiors of the first balloon 16 and the second balloon 20.

The internal partition 62 is preferably attached to the inside of the second balloon 20 and to the catheter shaft 12 at the central attachment site 34 prior to bonding the proximal end of the second balloon 20 and the distal end of the first balloon 16 to the catheter shaft 12.

Although only the steerable guidewire type internal partition tandem double balloon catheter is illustrated, bypass sidehole type and axial torque guidewire type catheters may also be made utilizing the internal partition design.

G. Tandem Triple Balloons/Overlap-Proximal

1. Steerable Guidewire Type

FIG. 21 schematically illustrates a triple balloon catheter using the type of overlap-proximal bonding illustrated in FIGS. 8 and 14. In this design, a third balloon has been added to the catheter. Thus, the tandem triple balloon catheter of FIG. 21 has a first balloon 16 on the catheter shaft 12. Proximally of the first balloon 16 is a second balloon 20, also on the catheter shaft 12, with the distal end of the second balloon 20 attached to the central attachment site 34 on the catheter shaft 12. The proximal end of the first balloon 16 is attached to the wall of the second balloon 20 proximally of the central attachment site 34 so that a part of the inflatable portion of the first balloon 16 is over the central attachment site 34. A third balloon 21 is provided on the catheter shaft 12. The distal end of the third balloon 21 is attached to the catheter shaft 12 at a second attachment site 74. The proximal end of the second balloon 20 is attached to the wall of the third balloon 21 proximally of the second attachment site 74 so that the second attachment site 74 is inside the inflatable portion of the second balloon 20. The first balloon 16 has the smallest maximum inflated diameter, the second balloon 20 has the next largest diameter, and the third balloon 21 has the largest maximum inflated diameter.

The addition of a third balloon to the catheter provides the catheter with the capability for performing triple vessel angioplasty with a single catheter. This catheter is potentially usable in triple vessel coronary angioplasty, but is perhaps better suited for angioplasty in the peripheral vascular system in which the vessels are long and tapered, and thus require different diameter balloons when multiple lesions are present in the same vessel. Of course, in the coronary vascular system, the vessels are relatively shorter and more tortuous.

The method of fabricating the tandem triple balloon catheter of FIG. 21 is the same as that used for the catheter of FIG. 15. Thus, the bonding techniques and the method of blowing the balloon segments would be the same. However, the catheter shaft 12 should be provided with not only the central lumen 22 for receiving the steerable guidewire, the first lumen 24 for inflating and deflating the first balloon 16 and the second lumen 26 for inflating the second balloon 20, it should also be provided with a third lumen 28 for inflating and deflating the third balloon 21.

2. Bypass Sidehole Type

The tandem triple balloon catheter of FIG. 21 advantageously may include proximal holes 70 in the catheter shaft 12 on the proximal side of the third balloon 21 and distal holes 72 on the distal side of the first balloon 16. These holes 70, 72 communicate with the central lumen 22 in the manner previously described to permit blood to bypass the balloons 16, 20, 21 by flowing through the central lumen 22 and the catheter shaft 12.

3. Axial Torque Type

As illustrated in FIG. 22, the tandem triple balloon design of FIG. 21 may be incorporated into an axial torque type catheter. In this design, the central lumen 22 does not extend completely through all three balloons 16, 20, 21, but instead terminates inside the first balloon 16. An axial torque guidewire extends through the central lumen 22 of the catheter shaft 12 and out of the distal end thereof. The distal end of the first balloon 16 is bonded to the axial torque guidewire 64, and the central lumen 22 is used for inflation and deflation of the first balloon 16. Separate radiopaque markers 32 may be provided in the center of each of the balloons 16, 20, 21. An overlap joint 60 is used to connect the first balloon 16 to the wall of the second balloon 20 and to connect the second balloon 20 to the wall of the third balloon 21 as discussed in connection with FIG. 8 and FIG. 21.

H. Tandem Triple Balloons/Overlap-Distal

1. Steerable Guidewire Type

The overlap-distal bonding of FIGS. 9 and 16 may be used in a triple balloon catheter as illustrated in FIG. 23. In this design, a distal first balloon 16, a central second balloon 20, and a proximal third balloon 21 are provided on the catheter shaft 12. The maximum inflated diameter of the second balloon 20 is greater than that of the first balloon 16, and the maximum inflated diameter of the third balloon 21 is greater than that of the second balloon 20.

The proximal end of the first balloon 16 is attached to the central attachment site 34, and the distal end of the second balloon 20 is attached to the wall of the first balloon 16 in an overlap joint 60. The proximal end of the second balloon 20 is attached to the catheter shaft 12 at a second attachment site 74, and the distal end of the third balloon 21 is attached to the wall of the second balloon distally of the second attachment site 74. Thus, part of the inflatable portion of the second balloon 20 is inside the third balloon 21, and part of the inflatable portion of the first balloon 16 is inside the second balloon 20. The inside portion 54 of the first balloon 16 that is inside the second balloon 20 may be of slightly reduced diameter to accommodate the increased thickness of the deflated second balloon 20 thereon. (This decrease in thickness has been exaggerated in the figures for illustration purposes only.) Similarly, the inside portion 76 of the second balloon 20 that is inside the third balloon 21 has a slightly reduced diameter as compared to the remainder of the second balloon 20 to accommodate the thicknesses of the overlying third balloon 21. The fabrication technique for this catheter is substantially the same as for the design illustrated in FIG. 16, except that in addition to the central lumen 22, extending through all three balloons 16, 20, 21, and the first and second lumens 24, 26, terminating, respectively, in first and second balloons 16, 20, the catheter shaft 12 also has a third lumen 28 extending therethrough and terminating inside the third balloon 21 for separate inflation and deflation thereof.

The diameter of the central lumen should be just large enough to accommodate a 0.018 inch guidewire, and should be large enough to monitor pressure through the central lumen while a 0.014 inch guidewire is in place. The outer diameter of the proximal catheter shaft 12 should be no larger than French size 4.7 for coronary applications.

In various embodiments, the portion of the first balloon 16 inside the second balloon 20 and the portion of the second balloon 20 inside the third balloon 21 may be at least 10%, at least 20%, at least 30%, at least 35%, or more than 35% but less than 80% or 85%. Increased "stacking" of the balloons in this manner can significantly reduce the length of the catheter occupied by the balloons 16, 20, 21. This catheter is better suited for coronary angioplasty than the design illustrated in FIG. 21, although at the same time it is well suited for peripheral angioplasty.

2. Bypass Sidehole Type

The balloon catheter of FIG. 23 may advantageously be provided with a plurality of proximal holes 70 on the proximal side of the third balloon 21 through the catheter shaft 12 into the central lumen 22 and with a plurality of distal holes 72 on the distal side of the first balloon 16 communicating with the central lumen 22. These holes 70, 72 can permit the flow of blood through the catheter shaft 12 past the balloons 16, 20, 21, as previously described.

3. Axial Torque Type

The axial torque type tandem triple balloon catheter of FIG. 24 utilizes the same overlap-distal joints between the first balloon 16, the second balloon 20, and the third balloon 21, as described previously in connection with FIG. 23. Unlike FIG. 23, however, the catheter shaft 12 terminates inside the first balloon 16 and an axial torque guidewire 64 extends from the end of the catheter shaft 12 through the first balloon 16 and out the distal end thereof. The distal end of the first balloon 16 is bonded to the axial torque guidewire 64. The central lumen 22 terminates inside the first balloon 16, and separate lumens 24, 26 are provided for inflating and deflating balloons 20, 21, respectively.

I. Tandem Triple Balloon/Overlap-Bridge

1. Steerable Guidewire Type

The triple balloon design illustrated in FIG. 25 is unique in that the third (and largest) balloon 21 is added to what is basically a separate tandem double balloon design. Thus, on the catheter shaft 12, there is provided a distal, first balloon 16, and a second balloon 20 located adjacent to the first balloon 16 and just proximally of the first balloon 16. The distal end of the second balloon and the proximal end of the first balloon 16 are bonded to the central attachment site 34. The first balloon 16 has the smallest diameter and the second balloon 20 has a larger diameter than the first balloon 16.

A third balloon 21, having a maximum inflated diameter larger than that of the second balloon 20, is also provided on the catheter. The distal end of the third balloon 21 is attached to the wall of the first balloon 16 distally of the central attachment site 34, and the proximal end of the third balloon 21 is attached to the wall of the second balloon 20 proximally of the central attachment site 34. The joints where the third balloon 21 attaches to the walls of the first and second balloons 16, 20 are overlap joints as illustrated in FIG. 9, and the portions of the first balloon 16 and the second balloon 20 inside of the third balloon 21 may be of reduced diameter to accommodate the thickness of the deflated balloon 21.

Fabrication of this catheter is similar, in principle, to the catheter of FIG. 16. The proximal end of the tube from which the first balloon 16 is to be blown and the distal end of the tube from which the second balloon 20 is to be blown are bonded to the central attachment site 34. Heat resistant tubes of metal, Teflon, or other suitable material are then slid inside the tubes that will form the first balloon 16 and the second balloon 20. The tube that will form the third balloon 21 is then positioned over the other two tubes and the ends are bonded to the first balloon 16 and the second balloon 20 in the desired location. The heat resistant material is then removed from inside the tubes that will form the first balloon 16 and the second balloon 20. The distal end of the first balloon 16 and the proximal end of the second balloon 20 are bonded to the catheter shaft, and then the balloons are blown. The first balloons 16 and the second balloon 20 are preferably blown in appropriately-shaped dies, after which the third balloon 21 is blown.

In the illustrated design, a central lumen 22 extends through all three balloons 16, 20, 21, with first, second, and third lumens 24, 26, and 28 communicating with the interiors of the first, second, and third balloons 16, 20, 21, respectively.

Bypass sideholes 70 on the proximal side of the second balloon 20 may be provided to communicate with the central lumen 22. Distal sideholes 72 may be provided through the catheter shaft 12 in communication with the central lumen 22 on the distal side of the first balloon 16. Upon balloon inflation, blood may bypass the balloons 16, 20, 21, by flowing through the central lumen in the catheter shaft 12.

Although not illustrated, an axial torque guidewire embodiment of the tandem triple balloon/overlap bridge design may be provided in which the catheter shaft 12 terminates inside of the first balloon 16 and an axial torque guidewire extends through the central lumen 22 and out of the distal end of the first balloon 16. The distal end of the first balloon 16 is bonded to the axial torque guidewire.

II. SURGICAL PROCEDURE

In connection with the new catheter designs set forth above, a surgical procedure utilizing those balloons to permit multi-vessel coronary or peripheral angioplasty in a greatly reduced time as compared to current techniques has been developed. This new percutaneous transluminal coronary angioplasty (PTCA) technique for multi-vessel disease is explained below in connection with a schematic drawing illustrating particular locations of cardiovascular disease. Of course, it will be understood that the precent technique can be utilized, in one form or another, with any of the catheter designs disclosed in the present application, and that utilization of the technique is not limited to the particular disease locations exemplified and illustrated in the following discussion and the accompanying Figure.

Figure 26:
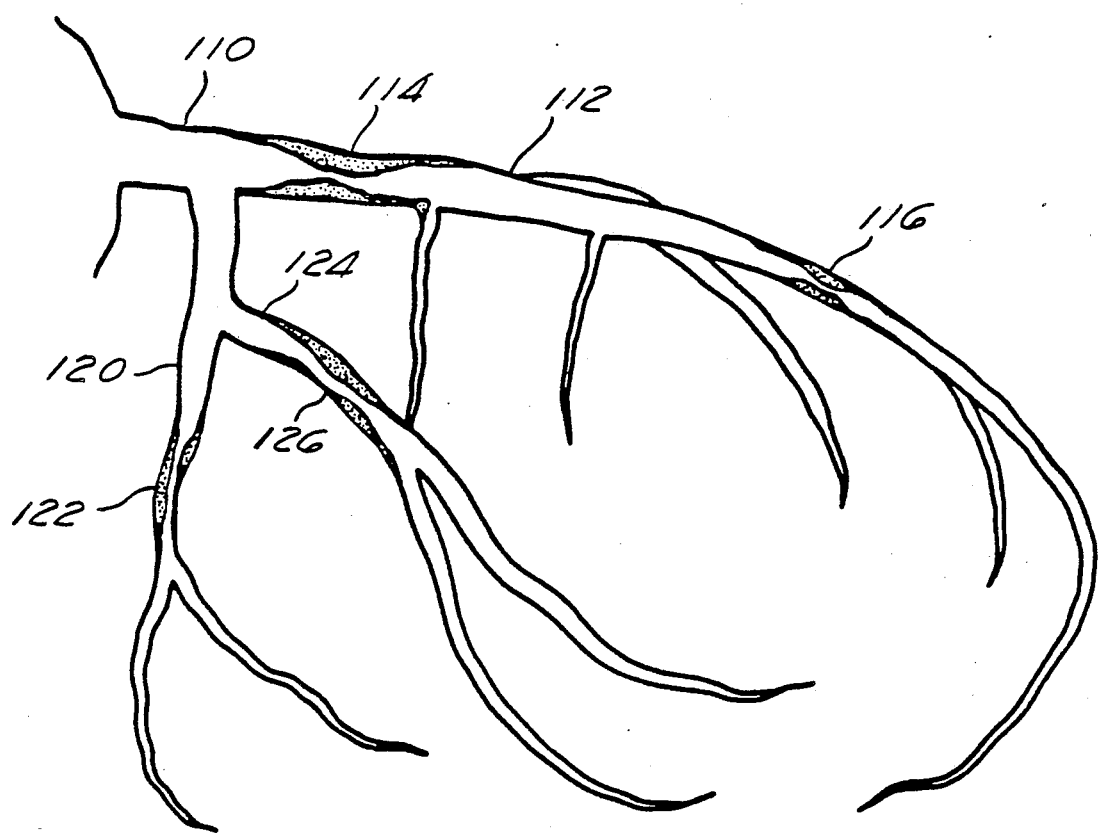
FIG. 26 is a diagram of the left coronary artery system.

A model of the left coronary system having multiple lesions in vessels of various diameter has been adopted for purposes of this description. The diagram used in this description, FIG. 26, represents a hypothetical but not unrealistic case. It should be understood, of course, that the new surgical technique described herein can be used in either the left or the right coronary artery, or in both arteries as a part of the same surgical procedure. What is critical for successful dilation of the lesions in question is that each dilation should be performed with a balloon having a predetermined maximum inflated diameter matching the native diameter of the artherosclerotic vessel.

FIG. 26 is a diagram of the left coronary artery system. The left main artery 110 branches into the left anterior descending (LAD) artery 112, in which two atherosclerotic lesions are illustrated. The first lesion 114 is located in the proximal portion of the LAD, in a vessel having a native diameter of 3.0 mm. The second lesion 116 is located in the distal LAD in a vessel having a native diameter of 2.0 mm. The circumflex artery 120 branches off of the left main artery 110. A third lesion 122 is illustrated in the circumflex artery 120, in a vessel having a native diameter of 2.0 mm. Finally, the obtuse marginal artery 124 (OMA) branches from the circumflex artery 120. A fourth lesion 126 is illustrated in the OMA 124 in a vessel having a native diameter of 2.5 mm.

With currently available PCTA techniques, three separate PCTA catheters would be needed for perform multivessel PTCA in this model. One of the catheters required would have a balloon of 3.0 mm, one a balloon of 2.5 mm, and one a balloon of 2.0 mm. With the procedure of the present invention, only one specially designed PCTA catheter is needed. As a result, the necessity for catheter exchange is eliminated, and the amount of X-ray exposure, the amount of contrast material injected, and the length of the PCTA procedure are all reduced.

The present invention may be used in the left coronary artery system having the lesions illustrated in FIG. 26 in the following way.

The patient is prepared and a conventional guiding catheter is inserted through the aorta into the left main artery 110. Any suitable triple balloon catheter of the type described previously herein is advanced through the guiding catheter and into the LAD 112. The triple balloon catheter is provided with a first balloon having a maximum inflated diameter of 2.0 mm, a second balloon having a maximum inflated diameter of 2.5 mm, and a third balloon having a maximum inflated diameter of 3.0 mm. Of course, all three balloons have been deflated with negative pressure as the catheter is advanced into the first lesion 114 in the LAD 112.

When the 3.0 mm third balloon is properly positioned inside the first lesion 114, as verified by radiography showing the location of the radiopaque marker inside the third balloon, the third balloon is selectively inflated while the other balloons remain collapsed. When proper dilation of the lesion 114 has been achieved, the third balloon is deflated by applying negative pressure to the third lumen. The balloon catheter is then advanced to the next target lesion with all three balloons completely deflated.

The balloon catheter is next advanced distally into the LAD 112 until the 2.0 mm first balloon is positioned inside the second lesion 116. Once the deflated 2.0 mm first balloon is centered in the second lesion 116, the first balloon is inflated to dilate the second lesion 116.

When the lesion 116 has been fully dilated by inflation of the first balloon, negative pressure is applied to fully deflate the first balloon. The catheter is then retracted back to the left main artery 110 and, through use of a steerable guidewire, is then threaded into the obtuse marginal artery 124. Because the fourth lesion 126 in the obtuse marginal artery 124 is in a vessel having a native diameter of 2.5 mm, the second balloon having a maximum inflated diameter of 2.5 mm is positioned inside the fourth lesion 126. The second balloon is then fully inflated to dilate the lesion 126, and is then collapsed as discussed in connection with the previous dilations. The catheter is then withdrawn from the obtuse marginal artery 124 and is inserted into the third lesion 122 in the circumflex artery 120. The third lesion 122, in a vessel having a native diameter of 2.0 mm, is dilated with the first balloon in the same manner as was described in connection with the second lesion 116.

The balloon catheter and the guiding catheter are then withdrawn and the procedure is completed in accordance with standard PCTA techniques.

Although the technique has been described in connection with the left coronary artery system, it is equally applicable in PTCA of the right coronary artery system and in peripheral angioplasty.

Because both the right and the left coronary artery systems are equally susceptible to atherosclerotic disease, often patients will have disease in both coronary arteries at the same time. As long as the lesions are accessible to balloon angioplasty, they may be conveniently and efficiently dilated by the technique described herein using the multi-balloon catheter. The same balloon catheter can be used in both arteries. However, it will typically be necessary to exchange the guiding catheter if the procedure involves a shift from one artery to the other. The principle of effective balloon catheter utilization is the same in the two arteries. However, in order to increase efficiency, guiding catheters changed from one artery to the other should be moved in such as way as to avoid a return to a vessel that has previously been entered. This is because each time the procedure is shifted from one artery to the other, it is necessary to exchange the guiding catheter.

The present invention permits full and effective dilation of some lesions that cannot effectively be dilated with a single balloon catheter. In some cases of advanced atherosclerotic disease, a lesion may result in such a reduced diameter that an angioplasty balloon having a maximum inflated diameter the same as the diameter of the native vessel cannot be advanced into the lesion. In this case, a multi-balloon catheter made in accordance with the present invention may be used to good effect. The low profile distal balloon on the catheter, having an inflated diameter less than the native diameter of the vessel, can be advanced into the lesion and inflated to partially dilate the lesion so that the appropriately-sized balloon can be placed inside the lesion and the lesion can be fully dilated. Thus, tight lesions can be predilated with a small balloon first, so that dilation of the lesions can be completed with the larger balloon. It is estimated that 20-25% of the single lesion cases in which balloon angioplasty is now performed currently require a second balloon catheter because the original-selected balloon catheter is too large to cross the lesion. With the present invention, these constricted single-lesion dilations can now be performed with a single multi-balloon catheter.

In summary, the procedure of the present invention requires advancing a multi-balloon angioplasty catheter of the type described herein having a plurality of differently-sized balloons into the vessel to be dilated, dilating a first lesion with a balloon having a first diameter, dilating a second lesion with a balloon having a second diameter, and, optionally, dilating a third lesion with a third balloon having a predetermined third diameter appropriate for the third lesion.

In accordance with another aspect of the procedure of the present invention, a single lesion may be dilated with a multi-balloon catheter of the type described herein by advancing a first balloon having a predetermined first diameter into the lesion, and dilating the lesion with the first balloon, and then advancing a second balloon into the lesion, wherein the second balloon has a maximum inflated diameter larger than the maximum inflated diameter of the first balloon, and then dilating the lesion with the second balloon.

What is claimed is:

1. A catheter for performing balloon angioplasty, comprising:

an elongate, flexible catheter shaft having a plurality of lumens therethrough;

a plurality of imperforate angioplasty balloons on said shaft, with the interior of each of said balloons in fluid communication with a different one of said lumens for separate inflation and deflation, each of said balloons having a predetermined maximum inflated diameter and being formed of non-elastomeric material, said balloons being capable of substantially maintaining said predetermined maximum inflated diameter at inflation pressures of 100 psi;

an axial torque guidewire extending through said catheter shaft and out of the distal end of said catheter shaft;

said balloons comprising:

a first balloon on said catheter shaft near the distal end thereof; and a second balloon on said catheter shaft proximally of and adjacent to said first balloon, wherein the maximum inflated diameter of said first balloon is less than the maximum inflated diameter of said second balloon, wherein the distal end of said first balloon is bonded to said guidewire and the proximal end of said first balloon is bonded to said shaft, said shaft terminating at the proximal end of said first balloon so that when said first balloon is deflated, the distal end of said catheter at said first balloon has a diameter less than the diameter of said shaft, such that when said second balloon is positioned in a stenosis in a branch of the left main artery system, and the first balloon extends into an artery of decreasing diameter, said first balloon does not occlude said artery.

2. The catheter of claim 1, wherein said first balloon and said second balloon are formed of a single, continuous tube of polymer material.

* * * * *